US010470710B2

(12) United States Patent
Bass et al.

(10) Patent No.: US 10,470,710 B2
(45) Date of Patent: Nov. 12, 2019

(54) SYSTEM FOR ACCURATE MEASUREMENT OF DYNAMICS AND KINEMATICS

(71) Applicant: Duke University, Durham, NC (US)

(72) Inventors: Cameron R. Bass, Durham, NC (US); Bruce P. Capehart, Chapel Hill, NC (US); Jason F. Luck, Durham, NC (US); Kyle A. Matthews, Durham, NC (US); Adam Mehlenbacher, Raleigh, NC (US); Jay Shridharani, Durham, NC (US)

(73) Assignee: Duke University, Durham, NC (US)

( * ) Notice: Subject to any disclaimer, the term of this patent is extended or adjusted under 35 U.S.C. 154(b) by 419 days.

(21) Appl. No.: 15/234,643

(22) Filed: Aug. 11, 2016

(65) Prior Publication Data

US 2016/0345903 A1 Dec. 1, 2016

Related U.S. Application Data

(63) Continuation-in-part of application No. PCT/US2015/015636, filed on Feb. 12, 2015.
(Continued)

(51) Int. Cl.
*A61B 5/00* (2006.01)
*A61B 5/01* (2006.01)
(Continued)

(52) U.S. Cl.
CPC .............. *A61B 5/6817* (2013.01); *A61B 5/01* (2013.01); *A61B 5/1114* (2013.01);
(Continued)

(58) Field of Classification Search
CPC . G06F 3/017; G06F 3/012; A61B 5/11; A61B 2562/0219; A61B 5/00;
(Continued)

(56) References Cited

U.S. PATENT DOCUMENTS 4,244,377 A * 1/1981 Grams ................. A61B 5/4863
128/865
5,539,935 A 7/1996 Rush, III
(Continued)

FOREIGN PATENT DOCUMENTS

WO 20050020841 A2 3/2005
WO 20080139404 A1 11/2008
(Continued)

OTHER PUBLICATIONS

International search report, International application No. PCT/US15/15636, dated May 21, 2015. ISA/US, Alexandria, VA.
(Continued)

*Primary Examiner* — May A Abouelela
(74) *Attorney, Agent, or Firm* — Olive & Olive, P.A.

(57) ABSTRACT

A sensor insert is provided for measuring head dynamics and kinematics. The sensor insert includes at least one sensor embedded in the insert. The insert is configured to fit relatively substantially immovably within a portion of a user's external auditory canal passing through the temporal bone. A system including the sensor and insert further includes an electronic data collection and processing unit connected to the sensor. A method of measuring head dynamics and kinematics involves use of the aforementioned system to detect and collect data measuring head dynamics and kinematics of a user's skull for analysis thereof.

19 Claims, 8 Drawing Sheets

Related U.S. Application Data (60) Provisional application No. 61/938,696, filed on Feb. 12, 2014.

(51) Int. Cl.
   *A61B 5/11* (2006.01)
   *A61B 5/1455* (2006.01)
   *A61F 11/08* (2006.01)

(52) U.S. Cl.
   CPC ........ *A61B 5/14552* (2013.01); *A61B 5/6843* (2013.01); *A61B 2562/0219* (2013.01); *A61F 2011/085* (2013.01)

(58) Field of Classification Search
   CPC ... A61B 5/0024; A61B 5/6803; A61B 5/6814; A61B 5/7405
   USPC ................ 600/300, 323, 407, 587, 595, 486
   See application file for complete search history.

(56) References Cited

U.S. PATENT DOCUMENTS

| | | | |
|---|---|---|---|
| 5,621,922 A | 4/1997 | Rush, III | |
| 6,077,237 A * | 6/2000 | Campbell | G06F 3/011 600/587 |
| 6,560,468 B1 * | 5/2003 | Boesen | H04M 1/0214 455/569.1 |
| 6,826,509 B2 | 11/2004 | Crisco, III et al. | |
| 6,925,851 B2 | 8/2005 | Reinbold et al. | |
| 6,941,952 B1 | 9/2005 | Rush, III | |
| 7,526,389 B2 | 4/2009 | Greenwald et al. | |
| 8,157,730 B2 * | 4/2012 | LeBoeuf | G06F 19/00 600/300 |
| 8,466,794 B2 | 6/2013 | Mack et al. | |
| 8,554,495 B2 | 10/2013 | Mack et al. | |
| 8,647,270 B2 * | 2/2014 | LeBoeuf | A61B 5/00 600/301 |
| 8,961,415 B2 | 2/2015 | LeBoeuf et al. | |
| 2004/0161445 A1 | 8/2004 | Bulk et al. | |
| 2004/0225236 A1 * | 11/2004 | Wheeler | A61B 5/1114 600/595 |
| 2005/0177335 A1 | 8/2005 | Crisco, III et al. | |
| 2005/0177929 A1 * | 8/2005 | Greenwald | A42B 3/046 2/425 |
| 2006/0015155 A1 * | 1/2006 | Charvin | H04R 25/606 607/57 |
| 2006/0189852 A1 | 8/2006 | Greenwald et al. | |
| 2007/0112287 A1 * | 5/2007 | Fancourt | A61B 5/1038 600/595 |
| 2007/0135717 A1 * | 6/2007 | Uenishi | A61B 5/02208 600/485 |
| 2008/0177162 A1 * | 7/2008 | Bae | A61B 5/02416 600/323 |
| 2009/0000377 A1 | 1/2009 | Shipps et al. | |
| 2009/0030350 A1 * | 1/2009 | Yang | A61B 5/1038 600/595 |
| 2009/0062686 A1 * | 3/2009 | Hyde | A61B 5/1112 600/558 |
| 2010/0331660 A1 * | 12/2010 | Wada | A61B 5/04 600/382 |
| 2011/0112355 A1 * | 5/2011 | Van den Heuvel | A61N 1/36036 600/25 |
| 2011/0206215 A1 * | 8/2011 | Bunk | G06F 1/1694 381/74 |
| 2012/0083688 A1 | 4/2012 | Nauman et al. | |
| 2012/0143526 A1 | 6/2012 | Benzel et al. | |
| 2012/0147009 A1 | 6/2012 | Benzel et al. | |
| 2012/0150453 A1 | 6/2012 | Benzel et al. | |
| 2012/0220893 A1 * | 8/2012 | Benzel | A42B 3/046 600/553 |
| 2013/0053823 A1 * | 2/2013 | Fiering | A61M 5/14276 604/514 |
| 2013/0216079 A1 * | 8/2013 | Nielsen | H04R 25/652 381/323 |
| 2013/0261377 A1 * | 10/2013 | Adamson | H04R 25/606 600/25 |
| 2013/0267766 A1 * | 10/2013 | Huber | A61F 5/58 600/23 |
| 2014/0029756 A1 * | 1/2014 | Galea | H04R 3/00 381/58 |
| 2014/0046192 A1 * | 2/2014 | Mullin | H05K 13/00 600/474 |
| 2014/0058220 A1 * | 2/2014 | LeBoeuf | A61B 5/0059 600/301 |
| 2014/0086424 A1 * | 3/2014 | Buehlmann | H04R 25/30 381/60 |
| 2014/0243617 A1 * | 8/2014 | LeBoeuf | A61B 5/0059 600/300 |
| 2014/0270210 A1 * | 9/2014 | van Dijk | H04R 25/70 381/60 |
| 2015/0038871 A1 * | 2/2015 | Hatzilias | A61B 5/4542 600/546 |
| 2015/0138556 A1 * | 5/2015 | LeBoeuf | A61B 5/0059 356/432 |
| 2015/0351688 A1 * | 12/2015 | Just | A61B 5/681 600/407 |

FOREIGN PATENT DOCUMENTS

| | | |
|---|---|---|
| WO | 20090152528 A1 | 12/2009 |
| WO | 20130170109 A1 | 11/2013 |

OTHER PUBLICATIONS

Panzer, M., et al., "Evaluation of Ear-Mounted Sensors for Determining Impact Head Acceleration." IRCOBI Conference, York, UK, Sep. 2009. pp. 319-322.

Extended European Search Report for European Patent Application No. 15748725.7, dated Oct. 2, 2017, 7 pages.

International Search Report and Written Opinion for International Patent Application No. PCT/US2015/015636, dated May 21, 2015, 7 pages.

International Preliminary Report on Patentability for International Patent Application No. PCT/US2015/015636, dated Aug. 25, 2016, 7 pages.

\* cited by examiner

SYSTEM FOR ACCURATE MEASUREMENT OF DYNAMICS AND KINEMATICS

CROSS REFERENCE TO RELATED APPLICATIONS

This application is a Continuation in Part of International Application Serial No. PCT/US2015/15636, filed Feb. 12, 2015 designating the United States and entitled, "A System for Accurate Measurement of Head Dynamics and Kinematics". The invention is also related to U.S. Provisional Application Ser. No. 61/938,696 entitled, "A System for Accurate Measurement of Head Dynamics and Kinematics" of the same inventors hereof, which was filed Feb. 12, 2014. The disclosures of International Application No. PCT US/2015/15636 and U.S. Provisional Application Ser. No. 61/938,696 are specifically incorporated by reference herein to the extent not inconsistent herewith, and Applicant claims priority to the filing dates of said International Application and said U.S. Provisional Application.

FIELD OF THE INVENTION

This invention relates to a sensor or multiple sensors embedded within an insert (the sensor embedded within an insert, and the multiple sensors embedded within an insert, are each interchangeably referred to as a "sensor insert" or an "insert"). The sensor insert is configured to be received within the external auditory canal of a user. The insert is sized and shaped to be received at a location in the external auditory canal passing against the temporal bone of a user's skull, i.e., the bony portion of the external auditory canal. The shape and configuration of the insert is such that the insert is in abutment with the temporal bone against the wall of a user's external auditory canal so as to be substantially immovable within the canal. The invention also relates to methods of measuring head dynamics and kinematics.

DISCUSSION OF EXISTING ART

Several existing types of head mounted technologies for measuring head movement involve sensors such as accelerometers mounted on helmets or mouthpieces. Another approach involves outer-ear based technologies for measuring head kinematics and dynamics and relies on coupling a measuring device either with the external auditory meatus (EAM) or the skin on the head, which are both movable relative to the skull bone.

The inventors have found that devices like these are inaccurate, with a large variance between the head kinematic or dynamic results reported or recorded by the device when compared to a reference device that is rigidly coupled to the skull. Recognition of this inaccuracy was not known and is important in determining impact dynamics for concussion and other applications of head dynamic and kinematic measurements. It is also important when determining vibration dynamics for use in determining human performance, or injury risk under vibration.

There have been other attempts to measure head motion, but all of the prior solutions suffer from the same defect. Each fails to adequately couple the measuring device to the head or skull. Failure to adequately couple the measuring device to the head or skull may be due to the mode of coupling, location of coupling or user interaction that reduces coupling.

Another known technique is disclosed in U.S. Pat. No. 8,554,495 which describes a system for analyzing head impact data. The system includes a sensor configured to be worn on the head of a user, for example, in a mouth guard which has been inserted into the mouth of a user. A limitation with such a system, as before, is that the sensor does not truly indicate the dynamics and kinematics of skull motion because the sensor can move within the mouth if not properly fit to the upper dentition of the user, or as a result of jaw or mouth motion associated with user behavior that degrades the coupling of the mouth guard over time or completely uncouples the mouth guard from the skull, to provide signals which are not indicative of true skull motion. U.S. Pat. No. 8,466,794 is similar to the aforementioned patent and suffers from the same disadvantages.

An alternative technology such as disclosed by U.S. Patent Publication 2012/0150453 describes placing sensors on an athlete, but does not specify the sensor locations and does not recognize that there can be relative movement of the sensor with respect to the skull as compared to the actual movement of the skull, and therefore does not account for these differences.

As an alternative approach to conventionally mounted sensors, U.S. Patent Publication 2012/0147009 contemplates a sensor mounted in a number of different locations and including as an implant secured to tissues of the body such as bone. Unfortunately, such implanted devices are not necessarily desirable because they require surgical intervention. As well, effectiveness depends on the location of placement. For example, in the case of a tooth implant placed in the lower jaw bone, the relative movement of the jaw would not necessarily result in signals indicative of true skull motion.

Yet another approach involves a scalp mounted sensor. However, as is readily apparent, a user's scalp can move relative to the skull introducing false signals to a sensor mounted either directly on the scalp or indirectly through a helmet, headband, or other device placed on the head.

The problem with all of these previously discussed methods and systems is that the sensor inserts are relatively moveable in relationship to the skull, or suffer from inadequate coupling to the skull, introducing additional translational and other kinds of movements which affect readings, introduce errors, and do not provide a true indication of dynamics and kinematics of skull movement, thus providing erroneous data for subsequent analysis such as, for example, for determining head injury parameters, motion parameters and vibration.

In accordance with the invention, the problems of relative movement of a sensor or sensors with respect to the skull with which they are associated to attempt to determine accurate skull dynamics and kinematics are avoided by providing a device and system in which a sensor or sensors can be mounted in the external auditory canal in a region where the auditory canal passes through the temporal bone of a user's skull (the bony portions of the canal) such that a sensor or sensors can be mounted within an insert configured to be in abutment with the temporal bone against a wall of the user's external auditory canal. This arrangement provides relative substantial immovability of the sensors relative to the skull.

BRIEF SUMMARY

In one aspect, the invention relates to a sensor insert for a user's ear measuring head dynamics and kinematics. The sensor insert includes at least one sensor embedded in the insert. The insert is shaped and sized to fit relatively substantially immovably relative to the skull within a portion of a user's external auditory canal passing through the temporal bone of a user's skull, i.e., the bony portion of the canal, and in abutment with the temporal bone against a flesh wall of the user's external auditory canal. More specifically, the sensor insert is in contact against the flesh wall of the auditory canal and indirectly through the wall in abutment with the temporal bone. Further, by the expression "substantially immovably" is meant that data collected closely tracks to that collected from sensors fixedly attached to a skull. In a more specific aspect, the insert can be molded by taking an impression of the user's external auditory canal at the desired location using technology much like is used in manufacturing hearing aids, such that an insert can be manufactured which results in a relatively tight custom fit within the bony portion of the external auditory canal.

The sensor insert may comprise a plurality of sensors adapted for connection to a data processing unit. In one specific embodiment, the sensor insert comprises at least one accelerometer but can alternatively comprise a plurality of sensors which include at least one accelerometer, and at least one of a gyroscope (interchangeably referred to as "angular rate sensor"), a temperature sensor and a pulse oximeter. A temperature sensor or pulse oximeter may serve, for example, to collect data which may be indicative of whether the insert has come partially or completely out of the ear.

In an alternative aspect, there is provided a sensor system which includes at least one sensor embedded in a sensor insert. The insert is configured to fit relatively substantially immovably within a portion of a user's external auditory canal passing through the temporal bone of a user's skull and in abutment with the temporal bone against a flesh wall of the user's external auditory canal. An electronic data collection and processing unit, which may include a power supply, analog to digital converter, integrated circuit communication, and/or data storage, is connected to the sensor insert.

In yet other specific aspects, both with respect to the sensor insert and with the sensor system, a passageway may be provided through the insert to allow sound to pass into the ear without impeding hearing in a substantial manner.

In yet still another aspect there is provided a method of measuring head dynamics and kinematics which includes placing the aforementioned sensor or sensors embedded within at least one insert within a portion of a user's external auditory canal at the temporal bone of the user, and with the sensor or sensors being connected to an electronic data collection and processing unit. Data are detected, collected, and digitized. The data are indicative of head dynamics and kinematics of the user's skull resulting therefrom and may be analyzed.

BRIEF DESCRIPTION OF THE DRAWINGS

Having briefly described the invention, the same will become better understood when read with reference to the appended drawings, wherein.

DETAILED DISCUSSION

In accordance with one embodiment of the invention, a system is provided which includes one or more sensors to measure one or more physiologically relevant parameters. The system includes, in one embodiment, a micro-electronics data storage processing unit and power supply. The system also includes the capability to transfer data to another device from the micro-electronic data storage and processing unit for further analysis. The sensors, data storage units, power supply and data transfer capabilities are combined in a manner known to those skilled in the relevant art.

Preferably the sensor insert is located in the external auditory canal ("EAC") at a location such that the insert is either fully within or well coupled to the bony portion of the canal at a location adjacent to the temporal bone of the skull of a user so as to be relatively substantially immovable with respect to the skull, and thereby capable of providing signals which are indicative of true skull motion.

More particularly, the system in accordance with the invention provides more accurate data through enhanced coupling to the skull of a user. The coupling ensures that there is less variability in motion of the sensors used relative to head motion.

In one embodiment, the sensor insert of the invention may be created from a casting of a mold taken of a user's external auditory canal. Thus, each sensor insert is specific to only one external auditory canal. The sensor inserts are not interchangeable between users nor interchangeable within the same user from left to the right external auditory canal, and the insert includes sensors that are embedded in the material making up the insert.

In another embodiment, sensor inserts are constructed in various sizes based on the variance of human ear canals. These various sizes serve to provide interchangeability between different external auditory canals while still providing substantial coupling to the bony portion of the canal at a location adjacent to the temporal bone of the skull of a user so as to be relatively substantially immovable with respect to the skull.

In one embodiment, a wire travels between at least one sensor within the insert and a data storage and processing unit, which also includes a power supply. More specifically, the power supply may be one of a number of types of power supplies, most simply a battery. Alternatively, wireless technologies may be used such that sensors within the insert connect wirelessly to a data storage and processing unit. The specific nature of wired or wireless connections are conventional and well known to those of ordinary skill in the art.

In one embodiment the sensor may be made of a material such as poly (methyl methacrylate) ("PMMA"). Alternatively, other materials may be used which are different and which may have a Young's modulus that is similar to PMMA, greater than PMMA, or less than PMMA, and selected for a particular user to ensure that the insert is received within the bony portion of the external auditory canal in a manner in which it is substantially immovable relative to the skull of a user.

As may be appreciated, PMMA is a transparent thermoplastic material often used as a lightweight or shatter-resistant alternative to glass. It is made from an acrylic acid and is a strong and lightweight material having a density of about 1.17-1.20 g/cm$^3$. It has good impact resistance. As may be appreciated by those of ordinary skill, while PMMA has been specified, it is not the only material that can be used to make the insert and other materials providing similar functionality in terms of creating a sensor insert that can be substantially immovably fitted within the ear can be employed as a substitute therefor.

In one specific implementation, the insert can be made using hearing aid technology for making hearing aids for a user's ear. In order to make a custom insert, an impression is taken of a user's external auditory canal. This impression is then used to make a mold or the impression is electronically scanned. The mold or scan is then used to produce a custom shell. Sensors appropriate for the applications are inserted into the shell and the shell is filled with a material to provide rigidity, for example, PMMA.

In another implementation, the insert can be made by directly embedding the sensor in a material shaped to the user's external auditory canal.

As may be appreciated, as an alternative, instead of using the impression or a scan thereof to produce a custom shell, a direct 3-dimensional scan of the auditory canal can be made without having to make a physical impression. The shell can then be made using the 3-dimensional scan. In either manner a sensor insert can be made which is shaped and sized to fit relatively substantially immovably relative to the skull within a portion of the user's auditory canal passing through the temporal bone.

Having generally provided a description of the invention previously, the same will be better understood with reference to the Figures.

Figure 1:
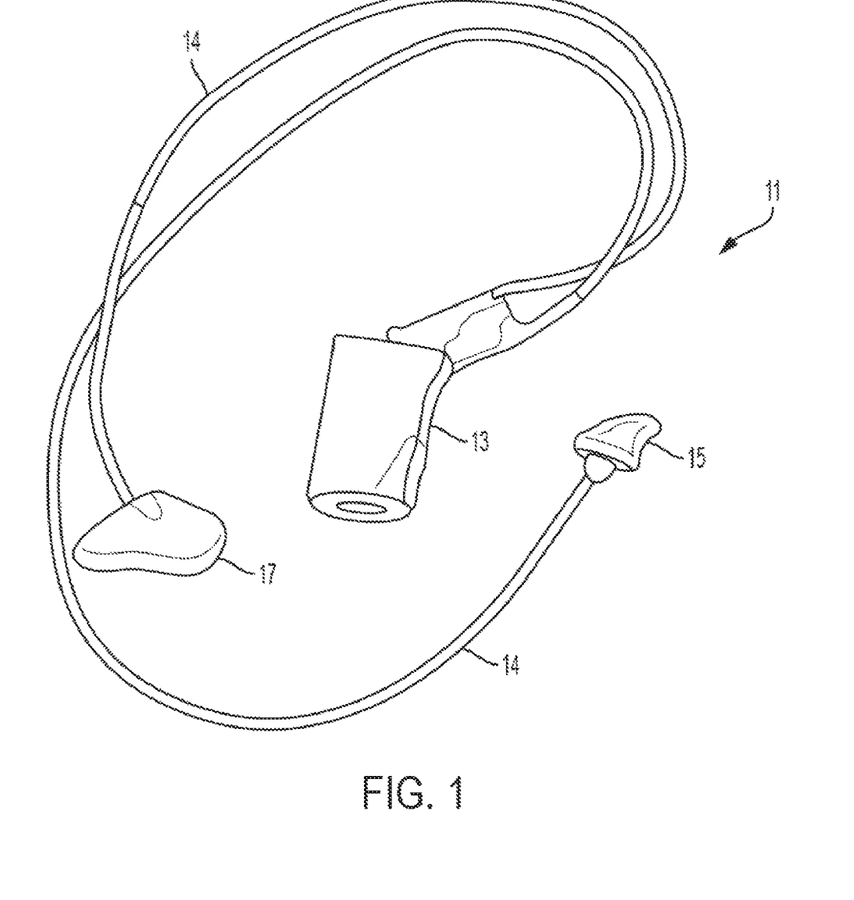
FIG. 1 is a perspective view of a two-ear system, including an ear-mounted data unit in accordance with the invention.

FIG. 1 is a perspective view of an embodiment of the system 11 of the invention for use with two ears and having an ear-mounted data collection and processing unit with a power supply 13. Two wires 14 are connected to the data collection and processing unit having a power supply 13, and lead to two sensor inserts 15 and 17, each configured for a specific user's right and left external auditory canals. As may be appreciated, in this embodiment, each of the sensor inserts 15 and 17 must be used with the respective corresponding external auditory canal for which it was molded, and cannot be interchanged. In one specific embodiment where PMMA is used, which is clear in nature, a dye can be added or other form of coloration to distinguish and to provide a different color for one insert when compared to the other, to ensure that when used the insert is placed in the correct external auditory canal.

Figure 2:
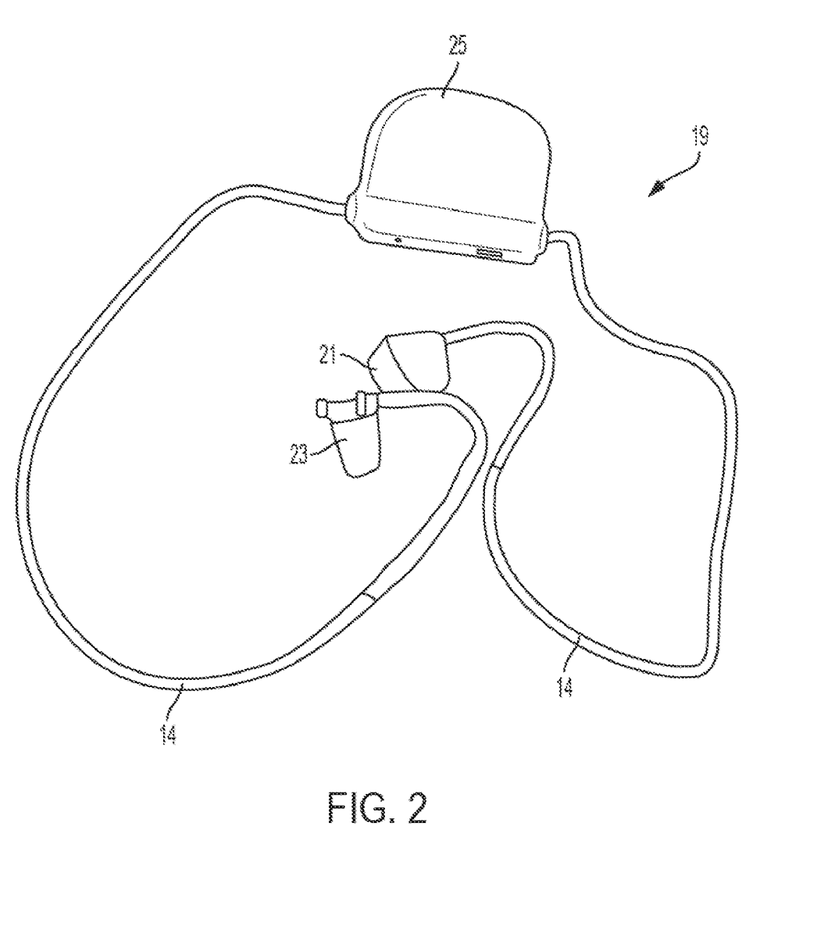
FIG. 2 is a perspective view of an alternative embodiment of the two-ear system of the invention showing a power supply and data processing unit of the type which is mountable on a helmet.

FIG. 2 illustrates an alternative embodiment of a system 19 to that of FIG. 1 where the sensor inserts 21 and 23, also connected through wires 14, are connected to a data collection and processing unit and power supply 25 which may be mounted on a helmet, or optionally on a headband, belt, or other portion of the user's clothing, accessories such as jewelry or watch, or body.

Figure 3:
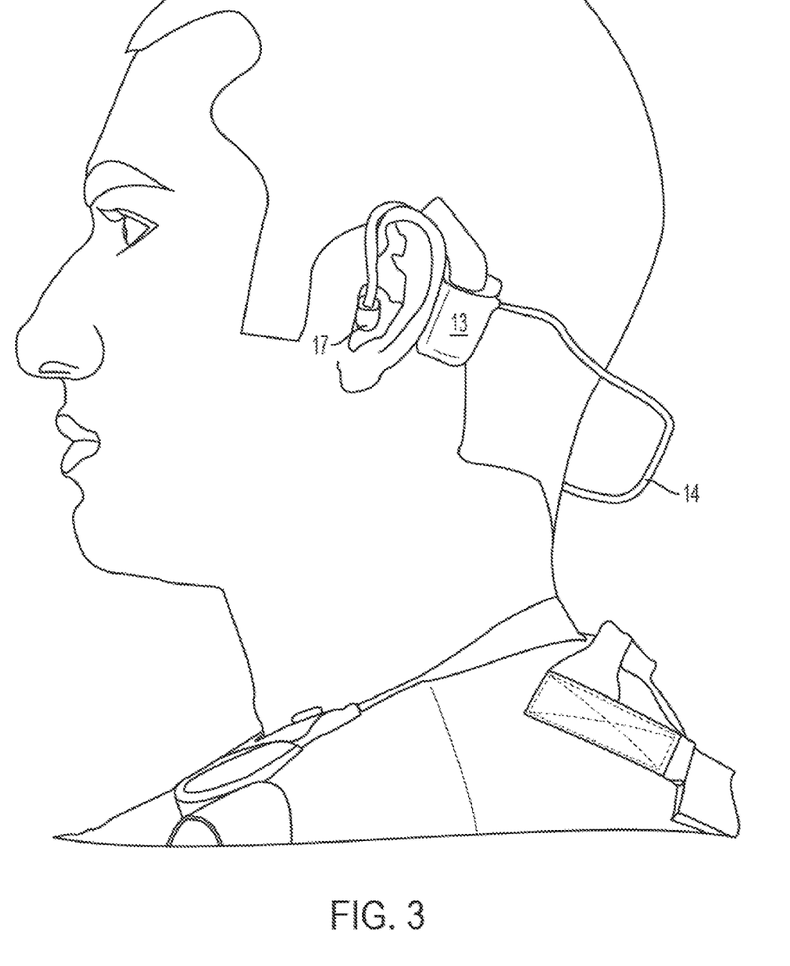
FIG. 3 is a side view of the embodiment of FIG. 1, shown worn by a user.
Figure 4:
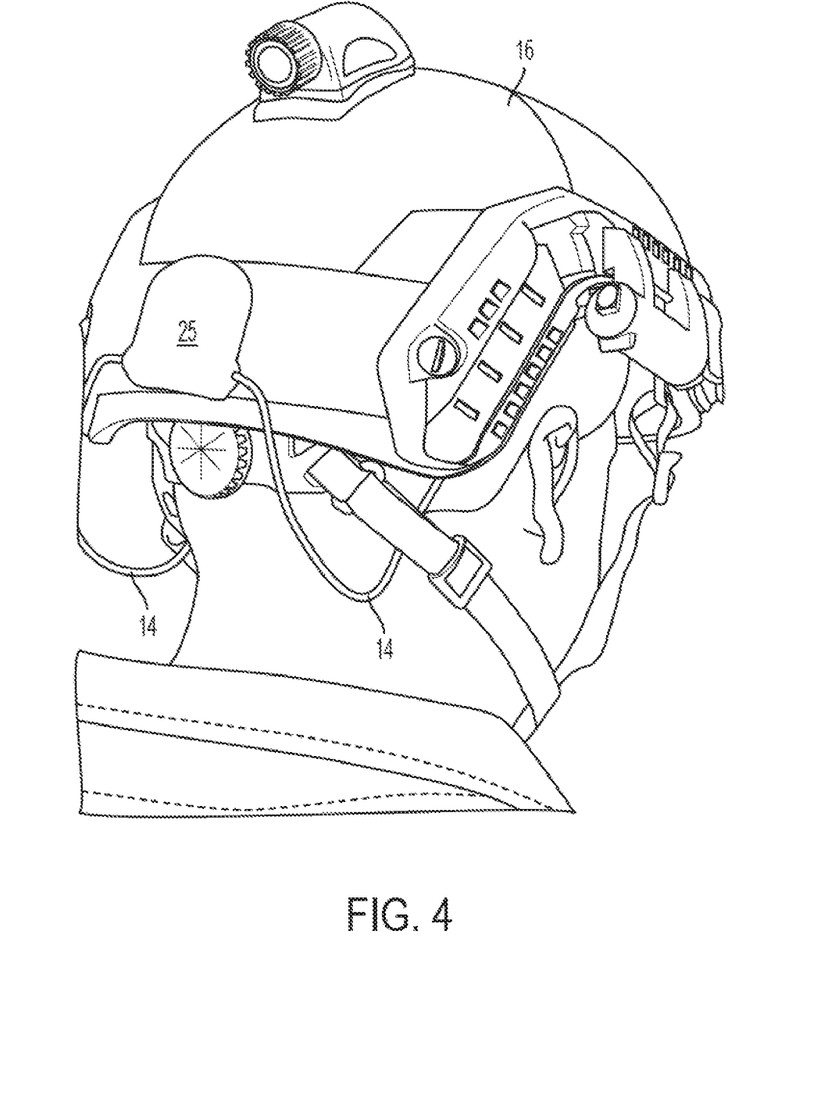
FIG. 4 is a perspective view of the system of FIG. 2 shown worn by a user with the data processing unit and power supply mounted on a helmet.

FIG. 3 shows the embodiment of FIG. 1 mounted on a user's head, and FIG. 4 shows the embodiment of FIG. 2 mounted on a helmet 16 of a user.

Figure 5:
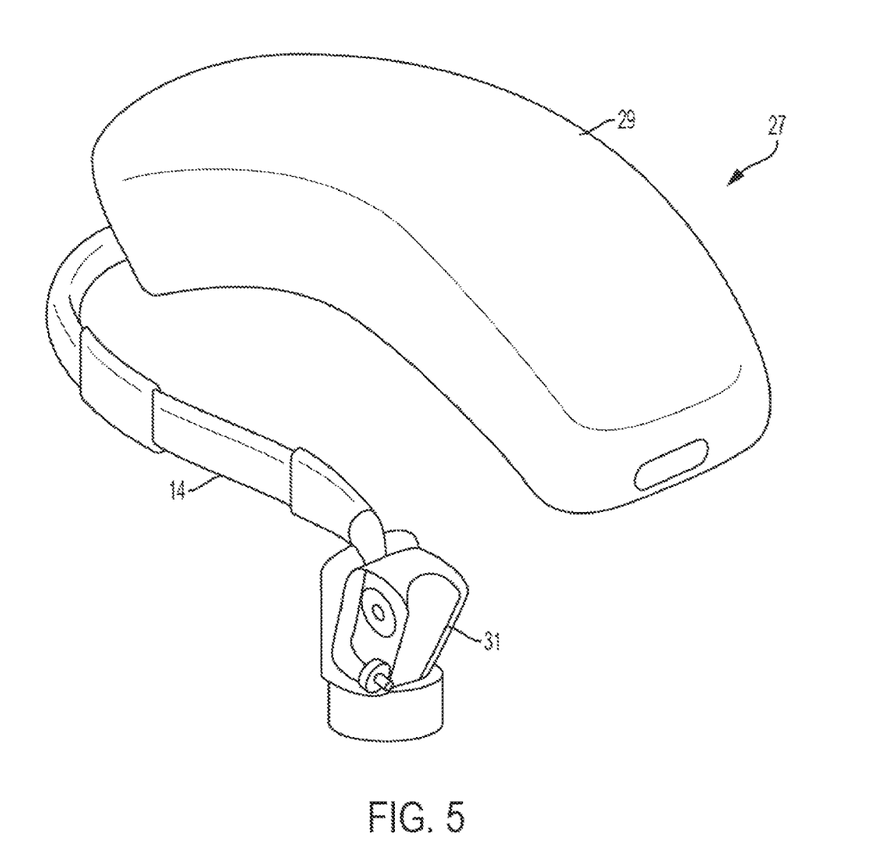
FIG. 5 is a perspective view of a one-ear embodiment in accordance with the invention.

FIG. 5 shows an alternative embodiment of the system 27 of the invention used for a single ear, and having a data collection and processing unit with a power supply 29 connected through a wire 14 to a sensor insert 31.

Figure 6:
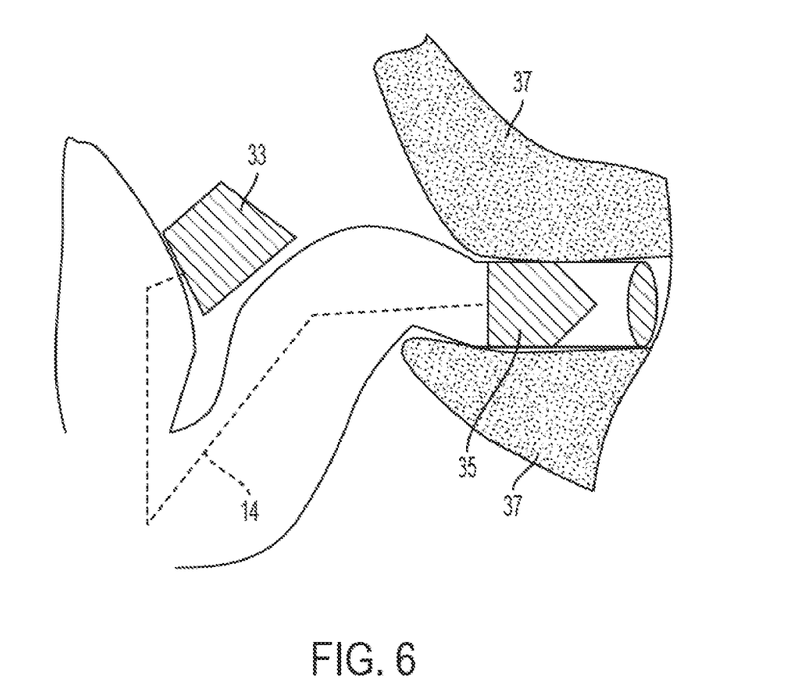
FIG. 6 is a schematic view showing a sensor insert in accordance with the invention inserted and mounted substantially immovably within the external auditory canal at a location in close proximity with the temporal bone of a user's skull.
Figure 7:
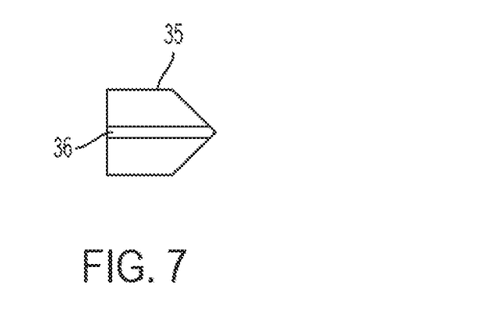
FIG. 7 is a schematic side view of a sensor insert as shown in FIG. 6, having a passageway therethrough to allow passage of sound.

FIG. 6 is a schematic diagram illustrating how the sensor insert of the invention fits within the bony portion of the external auditory canal at the bony portion thereof to be coupled in a substantially "press fit" arrangement with the temporal bone 37 of the skull through the flesh wall of the external auditory canal. The sensor insert 35 is shown in proximity to the temporal bone 37 with a wire 14 connected to an ear-mounted data acquisition and processing unit having a power supply 33. In an alternative embodiment as shown in FIG. 7, the sensor insert 35 can include a passageway 36 there through to allow for the passage of sound. In a specific aspect, if the passageway 36 is made of sufficient size, less than, for example, 3 dB of sound amplitude is attenuated as was achieved with one embodiment with a specific user. Further, alternative technologies will not necessarily require the passageway as the selection of the materials for the sensor insert 35 can be such as to allow for a material which allows the passage of sound therethrough without the requirement for a passageway 36.

Figure 8:
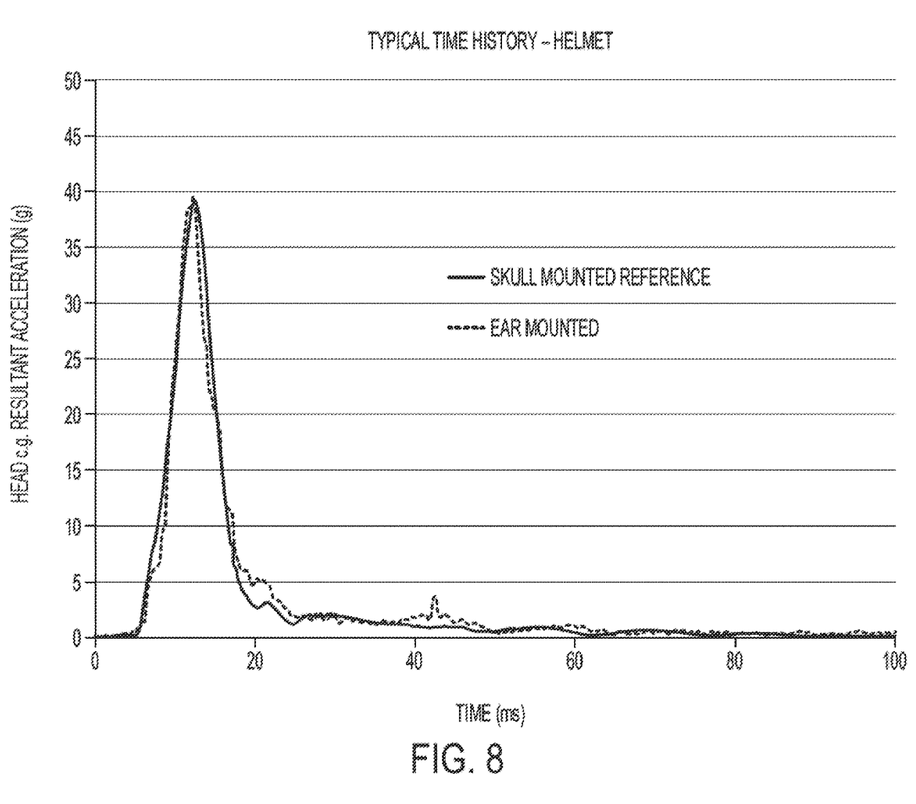
FIG. 8 is a time history graph comparing the performance of the ear-mounted substantially immovable insert of the invention to a skull mounted sensor dropped from a particular height, with the sensors attached fixedly to a cadaver skull.
Figure 9:
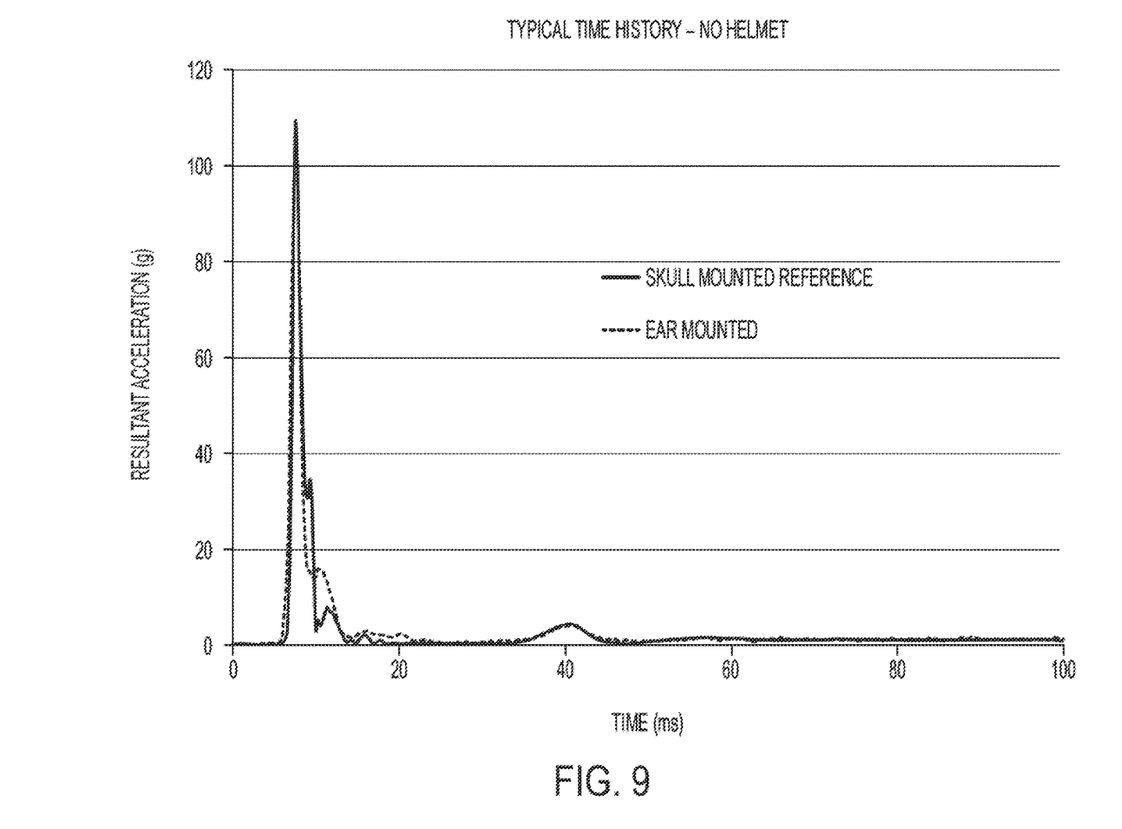
FIG. 9 is a graph like that of FIG. 8, but showing a second test conducted.

To verify the accuracy of measurements, tests were conducted with a sensor using three accelerometers and three gyroscopes mounted on a cadaver skull attached to the skull in a fixed manner to be immovable, and compared to an external auditory canal-mounted system of the invention. In FIG. 8 the test results are shown when a helmet was used on the specimen which was dropped from a fixed height onto a plate. FIG. 8 shows that the sensor detection achieved with the two devices tracked very closely to provide an accurate measurement of skull movement. FIG. 9 illustrates the results of a similar test for a similar test done without use of a helmet.

In terms of the sensors that can be used with the invention, as previously noted, an accelerometer may be used or a combination of various kinds of accelerometers with other types of sensors.

With respect to the data collection processing unit having a power supply, the power supply can be a battery such as a small lithium ion battery. The battery may power the data acquisition unit generally used to acquire, process, and store the data. The data acquisition unit may include a central processor, a digitizing unit, and integrated circuit communication. In one embodiment and in general terms the central processor can be conceived as a general purpose processor. The digitizing unit of the system is conventional and well known to those of ordinary skill in the art and takes an analog signal and converts it to digital form and samples it at various times. The times can be fairly fast as well known to those of ordinary skill in the art. The data is sampled and stored on nonvolatile or volatile memory. The memory can be a standard unit such as a standard SD card which is like memory for a home computer. Because memory is inexpensive and small, a large number of memory devices can be placed on the processing unit and at a later time, the data can be downloaded to a computer and further analyzed.

For definition purposes, by further analysis is meant analysis of the type of data acquired such as for characterizing head injuries or other types of activities affecting the head.

As may be also appreciated, the data acquisition and processing unit can be hung off of a user's ear, a helmet or sometimes clothing or a belt.

In terms of the sensors used, any number of combinations can be employed. For example, one or two accelerometers can be used, one in each ear or some combination of accelerometers in the ears in combination with gyroscopes. The accelerometers used in the inserts can be triaxial, but could also be four-axis or more with distributed small accelerometers within the ear canal. More specifically, there can be as many axes as may be specific to the application. In one current embodiment, a six-axis package is employed in a single ear implementation consisting of three linear accelerometers and three gyroscopes. More particularly, in order to capture data about an object that is simultaneously translating and rotating, such as a head, more than just three accelerometers are typically required, and frequently more than six.

While reference has been made to accelerometers, other types of sensors can be used in the system of the invention and include angular accelerometers, gyroscopes, temperature sensors and pulse oximeters. In the case of a temperature sensor, temperature can be monitored to determine whether the sensor insert has moved from its desired location within the bony portion of the external auditory canal.

Advantages of using a system such as described herein is that head impact data, including rotational and translational accelerations and velocities, can be reported as a magnitude and direction in all three spatial planes using accelerometers. Consistent results may be achieved without recalibrating the system. As a result of using the materials in accordance with the invention, the sensor insert can be cleaned after repeated use and the acrylic material or other material offer adequate protection for the sensors as the sensor insert is cleaned between use.

With the invention there is provided a portable device that can capture head kinematics and dynamics data throughout the day across a variety of occupational, recreational, sporting, military, or leisure activities, or even during sleep. By providing a wearable device, which may also be water resistant and/or hardened, the invention allows for continuous ambulatory measurement of head acceleration and/or movement under a multitude of conditions.

As already noted, the invention can be constructed with or without an opening in the sensor insert to allow hearing while worn. Potential applications include assessment of impact in sports or occupational settings where the wearer must also use hearing protection. Depending on sensors used, the invention could measure vibration exposure in occupational scenarios such as vibrating machinery.

Data from the system of the invention may be filtered using standard electronic or software-based techniques depending on the specific application. For example, a low pass filter can be applied to emphasize physiologically relevant frequencies for diagnosing and/or monitoring of neurologic disorders that typically occur under 50 Hz.

In one specific embodiment for making the insert, a radiographic image of the user's external auditory canal can be used to shape the sensor insert. Other techniques may involve photographs, laser scanning or alternative imaging techniques.

In a specific implementation, the sensor insert material is made of material having a Young's modulus greater than 100 GPa. The sensor insert may be coated with a different material to prevent the sensor material from direct contact with the skin of the external auditory canal within the temporal bone.

As already noted, while a wired implementation is shown, the sensors in the inserts can be designed to communicate wirelessly and the sensor insert can either fully occlude the auditory canal to provide hearing protection or not fully occlude the auditory canal to allow hearing. In another implementation, the device may include a microphone or speaker. In this manner, traffic or other kinds of sounds can be perceived by the user. Similarly, music can be transmitted into the ear from a source like a digital music player.

In an alternative embodiment, the sensor insert may be created from a material that can conform to the user's external auditory canal at the bony portion without custom molding fitting or modifications while still providing substantial coupling to the bony portion of the canal at a location adjacent to the temporal bone of the skull of a user so as to be relatively substantially immovable with respect to the skull In accordance with alternative uses of the system, an automated calibration for the sensors of the inserts can be provided since the sensor insert, after insertion, is unique to a specific auditory canal such that the location of the sensors and the sensor insert are directly mapped to the three spatial axes of the head.

The sensor insert may be made of a single material that surrounds the sensors in the sensor insert. Alternatively, it can be made of two or more materials that surround the sensors in the sensor insert. Yet still further, the sensor materials can be made as a structural construction of various materials in various configurations for a specific purpose.

While several different arrangements have been described herein, it will be appreciated by those of ordinary skill that a number of yet still different and alternative arrangements can be implemented to achieve the sensor insert, system and methods described in the preceding.

The foregoing details are exemplary only. Other modifications that might be contemplated by those of ordinary skill in the art are within the scope of this invention, and the invention is not limited by the examples illustrated herein.

What is claimed is:

1. A sensor insert for measuring head dynamics and kinematics, comprising:
   at least one sensor embedded in an insert configured to measure head dynamics and kinematics; and
   said insert configured to be a shape and size to fit substantially immovably in a user's auditory canal passing at least through part of a temporal bone of the user's skull in abutment with the temporal bone through contact with a wall of the user's at least one external auditory canal, and said at least one sensor being connectable to a data storage and processing unit.

2. The sensor insert of claim 1, wherein said insert has an exterior shape which is of the same shape as an interior of the user's external auditory canal, at a location within the auditory canal which passes at least in part through the temporal bone of the user's skull.

3. The sensor insert of claim 2, wherein said insert is made of a material having a Young's modulus sufficient to wedge the insert against tissue making up a wall of the external auditory canal, against the temporal bone of a user's skull in a manner to maintain the insert substantially immovable in relation to the user's skull.

4. The sensor insert of claim 1, wherein said at least one sensor comprises a plurality of sensors adapted for connection to the data storage and processing unit.

5. The sensor insert of claim 1, wherein said at least one sensor comprises at least one accelerometer.

6. The sensor insert of claim 1, wherein said at least one sensor comprises a plurality of sensors which comprise, at least one accelerometer, and at least one of an angular accelerometer, gyroscope, a temperature sensor, or a pulse oximeter.

7. The sensor insert of claim 1, wherein said insert further comprises a passageway therethrough configured to allow sound to be transmitted through the passageway into the user's external auditory canal to allow the user to hear.

8. A sensor system, comprising: at least one sensor embedded in an insert configured to measure head dynamics and kinematics; and
said insert configured to be a shape and size to fit substantially immovably in a user's auditory canal passing at least through part of a temporal bone of the user's skull in abutment with the temporal bone through contact with a wall of the user's at least one external auditory canal; and
an electronic data collection and processing unit connected to said sensor.

9. The sensor system of claim 8, wherein said insert has an exterior shape that is of the same shape as an interior of the user's external auditory canal at a location within the auditory canal which passes at least in part through at least a portion of the temporal bone of the user's skull.

10. The sensor system of claim 9, wherein said insert is made of a material having a Young's modulus sufficient to wedge the insert against tissue making up a wall of the external auditory canal, against the temporal bone of a user's skull in a manner to maintain the insert substantially immovable in relation to the user's skull.

11. The sensor system of claim 8, further comprising two sensor inserts, each uniquely configured to fit substantially immovably in corresponding external auditory canals of the user.

12. The sensor system of claim 8, wherein said at least one sensor comprises at least one accelerometer.

13. The sensor system of claim 12, wherein said at least one sensor comprises a plurality of sensors which comprise, in addition to said at least one accelerometer, at least one of an angular accelerometer, a gyroscope, a temperature sensor and a pulse oximeter.

14. The sensor system of claim 8, wherein said insert further comprises a passageway therethrough configured to allow sound to be transmitted through the passageway into the user's external auditor)' canal to allow the user to hear.

15. A method of measuring head dynamics and kinematics, comprising:
placing at least one sensor embedded in an insert within a portion of a user's external auditory canal passing through a temporal bone of the user's skull, the insert configured of a shape and size to fit substantially immovably in the user's auditory canal passing at least through a part of the temporal bone of the user's skull substantially said the portion of the canal passing through the temporal bone of the user's skull and in abutment with the temporal bone through contact with a wall of the user's external auditory canal:
connecting said sensor to an electronic data collection and processing unit; and
detecting and collecting data measuring head dynamics and kinematics of the user's skull resulting from movement of the skull with said electronic data collection and processing unit for analysis thereof.

16. The method of claim 15, further comprising placing said at least one sensor embedded in said insert in corresponding external auditory canals of the user.

17. The method of claim 15, wherein said at least one sensor comprises a plurality of sensors including at least one accelerometer.

18. The method of claim 17, wherein said at least one sensor comprises at least one temperature sensor or at least one pulse oximeter for detecting whether the sensor insert is outside or inside of the ear canal.

19. A sensor insert for measuring head dynamics and kinematics, comprising: at least one sensor embedded in an insert configured to measure head dynamics and kinematics;
said insert configured to be a shape and size to fit substantially immovably in a user's auditory canal passing at least through part of a temporal bone of the user's skull in abutment with the temporal bone through contact with a wall of the user's at least one external auditory canal;
said at least one sensor being connectable to a data storage and processing unit;
said at least one sensor comprises at least one accelerometer, at least one of an angular accelerometer, a gyroscope, a temperature sensor, and a pulse accelerometer, and said insert further comprising a passageway therethrough configured to allow sound to be transmitted through the passageway into the user's external auditory canal to allow the user to hear.

\* \* \* \* \*